United States Patent [19]

Sauer et al.

[11] Patent Number: 5,878,103
[45] Date of Patent: Mar. 2, 1999

[54] ADAPTIVE DETECTOR MASKING FOR SPEED-UP OF CONE BEAM RECONSTRUCTION

[75] Inventors: Frank Sauer; Supun Samarasekera, both of Princeton, N.J.

[73] Assignee: Siemens Corporate Research, Inc., Princeton, N.J.

[21] Appl. No.: 884,248

[22] Filed: Jun. 30, 1997

[51] Int. Cl.[6] ..................................................... A61B 6/03
[52] U.S. Cl. ............................................... 378/15; 378/94
[58] Field of Search ..................... 378/4, 15, 94

[56] References Cited

U.S. PATENT DOCUMENTS

| 5,333,164 | 7/1994 | Tam | 378/8 |
| 5,390,111 | 2/1995 | Tam | 378/16 |
| 5,390,226 | 2/1995 | Tam | 378/19 |
| 5,461,650 | 10/1995 | Tam | 378/4 |
| 5,463,666 | 10/1995 | Eberhard et al. | 378/4 |
| 5,504,792 | 4/1996 | Tam | 378/15 |

*Primary Examiner*—David P. Porta
*Assistant Examiner*—David Vernon Bruce
*Attorney, Agent, or Firm*—Lawrence C. Edelman

[57] ABSTRACT

A scanning and data acquisition technique for three dimensional (3D) computerized tomographic (CT) imaging of an object, wherein scanning at a plurality of positions along a source scanning trajectory causes an area detector to acquire cone beam projection data corresponding to a shadow of said object at each of scanning positions and Radon derivative data is calculated by processing line integral values from cone beam projection data. In order to improve the calculation efficiency of the Radon derivative calculation, calculation of the Radon derivative data uses a determination of the left and right boundaries of the shadow for each of the scanning positions, and calculates the Radon derivative data only using projection data from within the determined boundaries.

10 Claims, 2 Drawing Sheets

LEFT BOUNDARY    RIGHT BOUNDARY

LEFT BOUNDARY

RIGHT BOUNDARY

ADAPTIVE DETECTOR MASKING FOR SPEED-UP OF CONE BEAM RECONSTRUCTION

BACKGROUND OF THE INVENTION

1. Field of the Invention

The present invention relates generally to three-dimensional (3D) computerized tomography (CT) and more specifically, to a method and apparatus for improving the computational efficiency of an exact cone beam reconstruction.

2. Description of the Background Art

Recently a system employing cone beam geometry has been developed for 3D imaging that includes a cone beam x-ray source and a 2D area detector. An object to be imaged is scanned, preferably over a 360° angular range, either by moving the x-ray source in a scanning path about the object or by rotating the object while the source remains stationary. In either case, the area detector is fixed relative to the source, and relative movement between the source and object provides the scanning (irradiation of the object by the cone beam energy). The cone beam approach has the potential to achieve 3D imaging in both medical and industrial applications both rapidly and with improved dose utilization.

The 2D area detector used for 3D imaging generally has detector elements arranged in a 2D array of rows and columns. Available area detectors have generally been of large size and low quality, such as used with x-ray image intensifiers, or of small size and high quality. High cost and other factors have made large area 2D array detectors having high quality and high resolution, generally unavailable. In U.S. Pat. No. 5,390,112 entitled THREE-DIMENSIONAL COMPUTERIZED TOMOGRAPHY SCANNING METHOD AND SYSTEM FOR IMAGING LARGE OBJECTS WITH SMALL AREA DETECTORS issued Feb. 14, 1995, and hereby incorporated by reference, a cone beam CT system is disclosed in which an x-ray source following a spiral scan path is used to image a relatively long object, wherein the x-ray detector is much shorter than the object. The only height requirement for the detector is that it be longer than the distance between adjacent turns in the spiral scan of the x-ray source. As the cone beam source follows the scan path, the detector acquires many sets of cone beam projection data, each set representative of the x-ray attenuation caused by the object at each of the many source/detector positions along the scan path.

The cone beam projection data is then manipulated to reconstruct a 3D image of the object. The manipulation of the cone beam projection data is quite computationally complex and comprises:

1) conversion of the projection data to Radon derivative data. This may be generally be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference, 2) conversion of the Radon derivative data to Radon data at polar grid points using, for example, the technique described in U.S. Pat. No. 5,446,776 entitled TOMOGRAPHY WITH GENERATION OF RADON DATA ON POLAR GRID POINTS issued Aug. 8, 1995, also hereby incorporated by reference, and 3) performing an inverse 3D Radon transformation of the Radon data at the polar grid points using well known techniques, such as those described in detail in the fore-noted U.S. Pat. No. 5,257,183 for reconstructing image data that when fed to a display provides a 3D CT image of the object.

In view of the above computationally complex image data processing, efforts are needed for reducing the complexity.

Prior U.S. Pat. No. 5,333,164 entitled METHOD AND APPARATUS FOR ACQUIRING AND PROCESSING ONLY A NECESSARY VOLUME OF RADON DATA CONSISTENT WITH THE OVERALL SHAPE OF THE OBJECT FOR EFFICIENT THREE DIMENSIONAL IMAGE RECONSTRUCTION, issued Jul. 16, 1994 discloses a technique for reducing the amount of computation needed to make a 3D cone beam CT image by a priori knowledge of the aspect ratio of the object being imaged for reducing the points in Radon space that are sampled. Although this technique reduces computationally complexity, it would be desirable to reduce the required computations at an earlier stage of the reconstruction processing.

Prior U.S. Pat. No. 5,390,226 entitled METHOD AND APPARATUS FOR PRE-PROCESSING CONE BEAM PROJECTION DATA FOR EXACT THREE DIMENSIONAL COMPUTER TOMOGRAPHIC IMAGE RECONSTRUCTION OF A PORTION OF AN OBJECT, issued Feb. 14, 1995 discloses a technique for reducing the amount of computation needed to make a 3D cone beam CT image by attempting to retain for further processing that cone beam attenuation data acquired within a select region on the surface of the detector that provides projection data corresponding to beams actually attenuated by passing through the object. Thus, unnecessary detector data is discarded at the earliest possible opportunity of the image processing. However, the technique of U.S. Pat. No. 5,390,226, as illustrated in FIG. 2 (b) therein, only masks the detector data, i.e, reduces the projection data, by limiting the data used for further processing to that data between upper and lower projections of the object on the detector, i.e., the upper and lower boundaries of the "shadow" of the object. The projection data between the left and right boundaries of the object shadow and the left and right boundaries of the detector are not so limited, and in fact are ignored and assumed to not exist.

Since a practical CT imaging system is designed to image an object having a given maximum width, when the object being imaged is less than the maximum width, when using the technique of U.S. Pat. No. 5,390,226 there will be no useful projection data between the left and right boundaries of the object shadow and the left and right boundaries of the detector. It would be desirable if means were provided to actually determine the width of the object shadow in order to properly reduce the amount of data being processed.

Furthermore, if the actual object being imaged is not symmetric, as is the case, for example, with a medical patient, as the source/detector moves about the scan path, the width of the shadow will vary, resulting in a variable shadow width. The technique of U.S. Pat. No. 5,390,226 assumes a fixed width for the object shadow, requiring that a maximum permissible width be used to prevent the generation of image artifacts.

An object of the present invention is to reduce the computational complexity of 3D cone beam image reconstruction at the earliest possible stage in the reconstruction processing.

It is a further object of the invention to provide such reducing computation in an adaptive manner, thereby maximizing the efficiency of the image reconstruction processing.

SUMMARY OF THE INVENTION

In accordance with the principles of the present invention, for each set of detector data, the right and left boundaries of the object's projection are determined in a pre-processing step. Consequently, later in the reconstruction processing, only those line integrals which contain actual information are carried out, thereby speeding-up the exact cone beam reconstruction algorithm.

More specifically, means are provided for determining the area on the detector which is covered by the width of the object's projection. Based on this knowledge, each integration line is checked to determine if it intersects the projection of the object. If it is determined that the corresponding integral would not contain any relevant information, that line integration is not performed.

Furthermore, the efficiency of the calculation of the line integrals which do contain valid object information is also improved. This is possible by shortening the integration line and integrating the projection data only over the length of the line which lies inside the actual projection of the object on the detector. The narrower the object being imaged, the greater the increase in efficiency for calculating the line integrals.

The present technique is highly efficient and reduces the computations required for objects having a width that is less than the maximum width that can be imaged. Additionally, the present technique is adaptive to the changing shape of the object's projection on the detector, further increasing the computational efficiency. In comparison, the computational cost of the standard implementation is fixed at a relatively high level as determined by the largest possible width of the projection of the object.

DETAILED DESCRIPTION OF THE PREFERRED EMBODIMENTS

Figure 1:
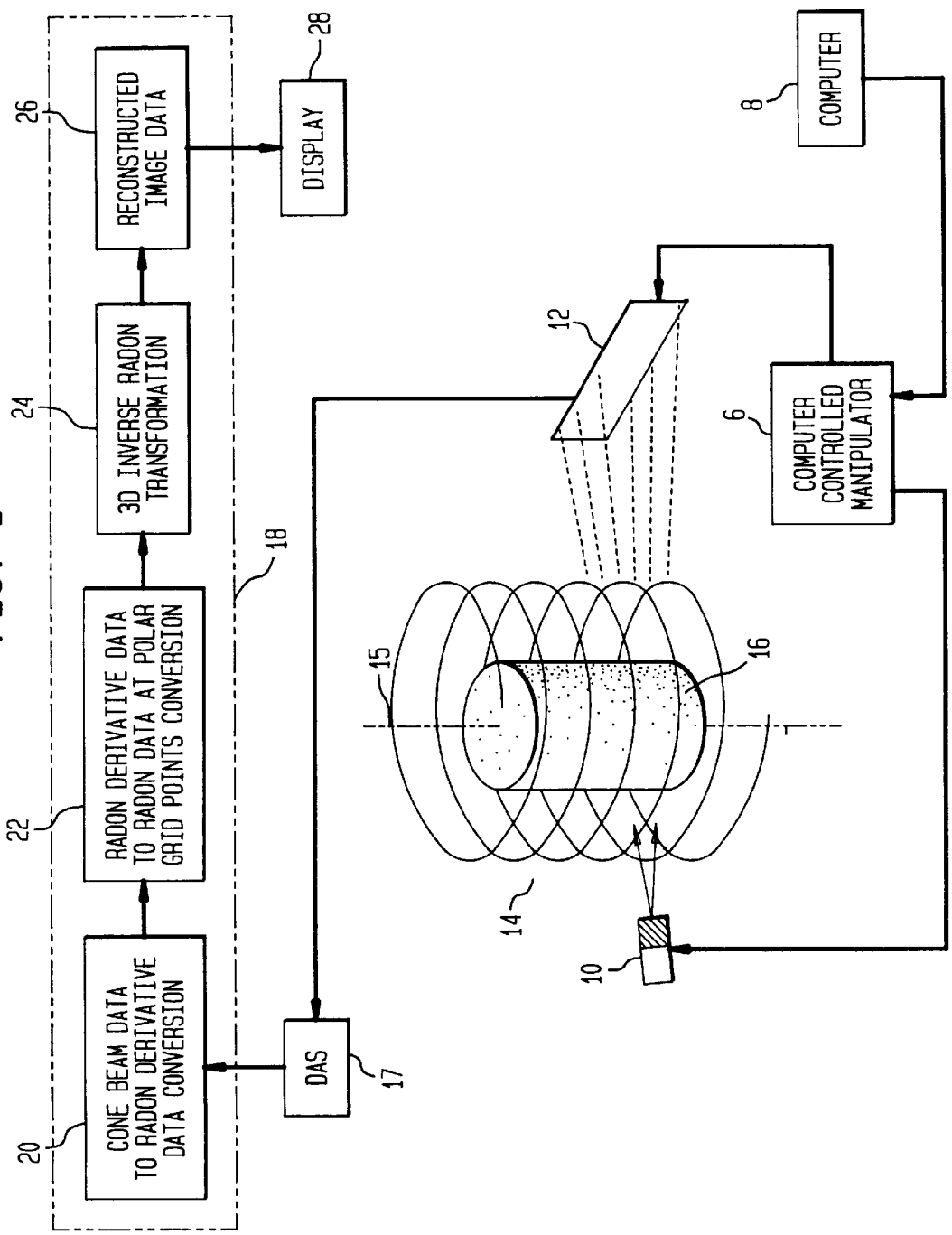
FIG. 1 is a simplified perspective illustration of the imaging of an object using an x-ray source and detector, combined with a simplified block diagram of image reconstruction according to the present invention.

FIG. 1 illustrates a cone beam 3D CT imaging system useful for carrying out the present invention, which is substantially the same, except as to be specifically described later, as known in the forenoted U.S. Pat. No. 5,390,112. As illustrated, a computer controlled manipulator 6, in response to control signals from an appropriately programmed computer 8, cause a source of cone beam energy 10 and a two-dimensional array detector 12 to cooperate along a defined source scanning trajectory, illustrated as a spiral scan path 14 centered on a predetermined axis 15 of an object 16, allowing detector 12 to acquire complete cone beam projection data for eventual reconstruction of an image of object 16. Computer 6, manipulator 8, source 10 and detector 12 cooperate in a manner generally well understood by those skilled in the art, i.e., such as described in detail in my forenoted U.S. Pat. No. 5,390,112, and therefore further details of their operation is not necessary. Alternatively, and equivalently, object 16 could be rotated to cause scanning by a fixed position source and detector. Furthermore, the scanning can be accomplished in a continuous or stepwise manner, and the spiral path can have equally spaced turns (sometimes referred to as stages), or turns with increasing pitch at the top and bottom edges of a region of interest of the object. Furthermore, although source 10 is shown as an x-ray source, other types of imaging energy might be used, such as neutrons, positrons, etc.

Signals corresponding to the sensed x-ray energy falling on elements within detector 12 are supplied to a data acquisition system (DAS) 17 which, like the previously described portions of FIG. 1, may operate in a fashion well known to those of ordinary skill in this technology for digitizing, pre-processing, and storing of the cone beam projection data.

Cone beam projection data from the DAS 17 is supplied to a processor 18, which may be a computer programmed to perform various data conversions illustrated by the blocks within the processor 18. At block 20 the cone beam data is converted to Radon derivative data. This may be generally be accomplished using the techniques described in the forenoted U.S. Pat. No. 5,257,183. At block 22 the Radon derivative data is converted to Radon data at polar grid points using, for example, the technique described in the forenoted U.S. Pat. No. 5,446,776. The Radon data at the polar grid points is supplied to block 24 which performs an inverse 3D Radon transformation using well known techniques, such as those described in detail in the forenoted U.S. Pat. No. 5,257,183. At block 26 reconstructed image data is developed, and then fed from processor 18 to a display 28, which may operate in known fashion, to provide 3D CT imaging of object 16.

A more detailed description of the blocks of FIG. 1 can be found in the forenoted patents incorporated by reference herein.

As previously forenoted, the exact cone beam reconstruction algorithm as described in U.S. Pat. No. 5,257,183 is based on the calculation of line integrals to determine the Radon transform of the x-rayed object. The line integrals are performed on the projection data provided by the 2-D detector. The size of this detector determines the maximum width of the object.

In a straightforward implementation of the algorithm, one calculates all the line integrals necessary to fill up the Radon support corresponding to this largest possible object. A real object, however, would usually be smaller than the maximal allowable one. Furthermore, when we think of a human patient, the "object" would also exhibit smaller and larger widths for different projections as it is non-cylindrical.

To calculate the full, standard Radon support for such objects is inefficient since one spends time calculating and processing Radon points which contain no information about the image of the object.

In accordance with the principles of the present invention, before calculating the line integral data necessary for developing the Radon derivative data (block 20) for each projection image, the extent of the object projection on the detector, e.g., it's left and right boundaries, are determined. Once determined, only line integrals need to calculated that intersect the actual width of the projection data. Furthermore, one may even speed-up the calculation of the integrals which do contain valid object information. This is possible by shortening the integration line (i.e., adjusting it's start and end points) so as to integrate projection data only over the part of the line which lies inside the object's projection.

Figure 2:
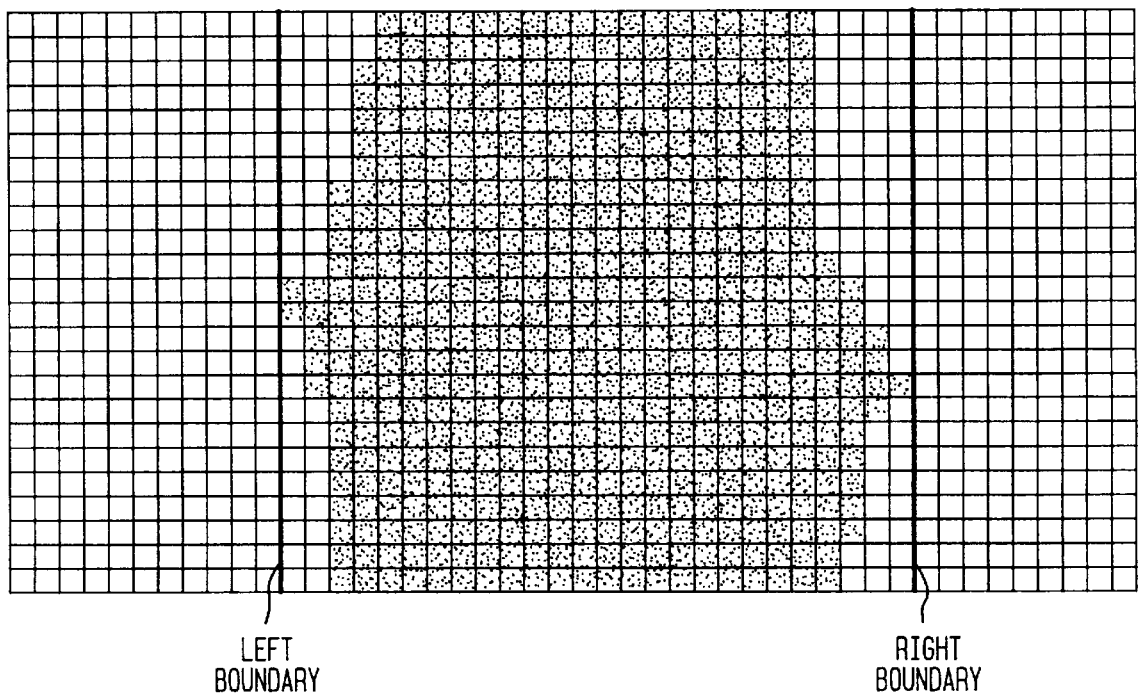
FIG. 2 illustrates a pixelated detector having object projection data therein, useful for describing the present invention.

FIG. 2 illustrates a pixelated detector having object projection data therein, useful for describing the present invention.

One efficient technique for finding the width of the object's projection is:

1) Check the value of the projection data through one row of pixels (e.g. the top row of the detector), from left to right, until data representative of the object is first encountered (as determined by sensing a value for the projection data that is non-zero). This position is easy to recognize since the contrast between outside and inside of an object (human patient) is strong.

2) From the first encounter, we move back towards the left edge of the detector, now calculating the sum of the projection data over each column of pixels. Assuming the values outside the object are substantially zero, we progress until we encounter the first vertical sum with a value of (about) zero. This corresponds to the left boundary of the projection of the object.

The same procedure, in reverse directions, starting from the right edge of the image, can be used to determine the right boundary of the projected object.

Performing the vertical summation of the projection data is a fast process and could be implemented in hardware. The assumption of values of zero outside the projection is reasonable for practical situations. Due to noise, however, one needs to use a small non-zero threshold when deciding whether a particular column of pixels is completely outside the projected object or not.

The above technique can be simply carried out as a pre-processing step (i.e., before block 20), by DAS 17.

Thus, there has been shown and described a novel method and apparatus for speeding up the reconstruction of an image in a cone beam 3D CT imaging system. Many changes, modifications, variations and other uses and applications of the subject invention will, however, become apparent to those skilled in the art after considering this specification and its accompanying drawings, which disclose preferred embodiments thereof. For example, after finding one of the boundaries of the object's projection, one could continue to sense projection data along the same row until the opposite boundary is found.

Furthermore, although in the illustrated embodiment the left and right boundaries are determined as straight lines, one could examine the object's projection on a row-by-row basis to form contoured left and right boundaries.

Additionally, although in this illustrated embodiment DAS 17 pre-processes the projection data to determine the left and right boundaries, a simple analysis of line integrals that are only vertically oriented on the detector can easily indicate the left and right boundaries, and in fact is equivalent to the forenoted summation of the columns of projection data.

All such changes, modifications, variations and other uses and applications which do not depart from the spirit and scope of the invention are deemed to be covered by this patent, which is limited only by the claims which follow as interpreted in light of the foregoing description.

What is claimed is:

1. A scanning and data acquisition method for three dimensional (3D) computerized tomography (CT) imaging of an object in a field of view radially centered on a predetermined axis, the method comprising the steps of:

applying cone beam energy from a cone beam source to at least a portion of the object;

defining a source scanning trajectory as a path traversed by the source;

using the cone beam source, fixed relative to an area detector with both source and detector movably positioned relative to the object, to scan about the object;

specifying the source scanning trajectory as a spiral path defining a plurality of spaced stages on a predetermined geometric surface surrounding the field of view such that each plane passing through the field of view intersects the scanning trajectory in at least one point and intersects the area detector, the area detector comprising a plurality of detector elements arranged in an array of rows and columns and having a height that extends sufficiently along a direction generally parallel to the predetermined axis so as to span at least two consecutive stages of the spiral path having the largest spacing therebetween;

scanning at a plurality of positions along the source scanning trajectory to cause the detector elements of said area detector to acquire cone beam projection data corresponding to a shadow of said object on the detector at each of said scanning positions;

calculating Radon derivative data by processing line integral values from the cone beam projection data acquired at each of said scanning positions; and reconstructing an image of the object using said Radon derivative data;

wherein said step of calculating Radon derivative data includes a preliminary determination step for determining left and right boundaries of said shadow on the detector at each of said scanning positions, and then excluding cone beam projection data determined to be outside said left and right boundaries when calculating said Radon derivative data.

2. The method of claim 1, wherein said determination step is carried out by a pre-processing step before any processing of line integral values by said calculating step.

3. The method of claim 1, wherein said determination step is carried out during said calculating step by calculating a plurality of vertical line integrals for each object projection, and analyzing said vertical line integrals to determine the left and right boundaries.

4. The method of claim 1, wherein said determination step determines left and right boundaries as straight vertical lines.

5. The method of claim 1, wherein said determination step determines left and right boundaries as curved vertical lines.

6. A scanning and data acquisition apparatus for three dimensional (3D) computerized tomography (CT) imaging of an object in a field of view radially centered on a predetermined axis, comprising:

means for applying cone beam energy from a cone beam source to at least a portion of the object;

means for defining a source scanning trajectory as a path traversed by the source;

means for using the cone beam source, fixed relative to an area detector with both source and detector movably positioned relative to the object, to scan about the object;

means for specifying the source scanning trajectory as a spiral path defining a plurality of spaced stages on a predetermined geometric surface surrounding the field of view such that each plane passing through the field of view intersects the scanning trajectory in at least one point and intersects the area detector, the area detector comprising a plurality of detector elements arranged in an array of rows and columns and having a height that extends sufficiently along a direction generally parallel to the predetermined axis so as to span at least two consecutive stages of the spiral path having the largest spacing therebetween;

means for scanning at a plurality of positions along the source scanning trajectory to cause the detector elements of said area detector to acquire cone beam projection data corresponding to a shadow of said object on the detector at each of said scanning positions;

preliminary processing means for determining left and right boundaries of said shadow on the detector at each of said scanning positions; and reconstruction processing means for processing acquired cone beam projection data for reconstructing an image of the object, said reconstruction processing means being responsive to the left and right boundaries of said shadow as determined by said preliminary processing means, for excluding cone beam projection data that is outside the determined left and right boundaries, when processing cone beam projection data for reconstructing the image.

7. The apparatus of claim 6, wherein said reconstruction processing means calculates Radon derivative data by processing line integral values from the cone beam projection data acquired at each of said scanning positions, said line integrals having a length in the cone beam projection data that is determined by the left and right boundaries of each shadow.

8. The apparatus of claim 6, wherein said preliminary processing means calculates a plurality of vertical line integrals in the cone beam projection data acquired at each of said scanning positions, and analyzes said vertical line integrals to determine the left and right boundaries of each shadow.

9. The apparatus of claim 6, wherein said preliminary processing means determines the left and right boundaries as straight vertical lines.

10. The apparatus of claim 6, wherein said preliminary processing means determines the left and right boundaries as curved vertical lines.

* * * * *